United States Patent [19]
Bab et al.

[11] Patent Number: 5,874,677
[45] Date of Patent: Feb. 23, 1999

[54] DEVICE AND METHOD FOR THE ULTRASONIC DETECTION OF DENTAL CARIES

[75] Inventors: Itai Bab, Karmei Yossef; Osnat Feuerstein, Jerusalem, both of Israel

[73] Assignee: Novadent Ltd., Jerusalem, Israel

[21] Appl. No.: 777,804

[22] Filed: Dec. 31, 1996

[30] Foreign Application Priority Data

Nov. 26, 1996 [IL] Israel ........................................ 119701

[51] Int. Cl.⁶ .................................................. G01N 29/10
[52] U.S. Cl. ............................ 73/629; 073/598; 073/632; 073/644; 433/215; 600/437
[58] Field of Search ............................ 73/629, 632, 642, 73/644, 627, 598, 600; 128/660.01–600.07; 433/215; 600/437

[56] References Cited

U.S. PATENT DOCUMENTS

| | | | |
|---|---|---|---|
| 4,373,401 | 2/1983 | Baumoel | 73/644 |
| 4,637,256 | 1/1987 | Sugiyama et al. | 73/633 |
| 5,100,318 | 3/1992 | Demyun et al. | 128/660.06 |
| 5,115,813 | 5/1992 | Ylander et al. | 128/660.01 |

FOREIGN PATENT DOCUMENTS 928810  6/1983  Japan .

*Primary Examiner*—Hezron Williams
*Assistant Examiner*—Nashmiya Fayyaz
*Attorney, Agent, or Firm*—Frommer Lawrence & Haug LLP; William S. Frommer; Matthew K. Ryan

[57] ABSTRACT

A device for the detection of smooth surface lesions of dental caries on a tooth crown surface, having an ultrasonic transducer for transmitting ultrasonic waves and receiving ultrasonic wave reflections produced by lesions present on the surface, and an interface operatively connected to the transducer. The interface has a contact surface forming an angle α with a longitudinal axis of the ultrasonic transducer, where α is substantially different from 90°. When the contact surface is in at least partial contact with a tooth crown surface at the longitudinal axis, ultrasonic waves generated by the ultrasonic transducer are imparted by the interface onto the tooth crown surface as surface ultrasonic waves which migrate along the tooth crown surface. Any lesions present on the tooth crown surface are then identifiable as surface ultrasonic wave reflections produced thereat.

46 Claims, 6 Drawing Sheets

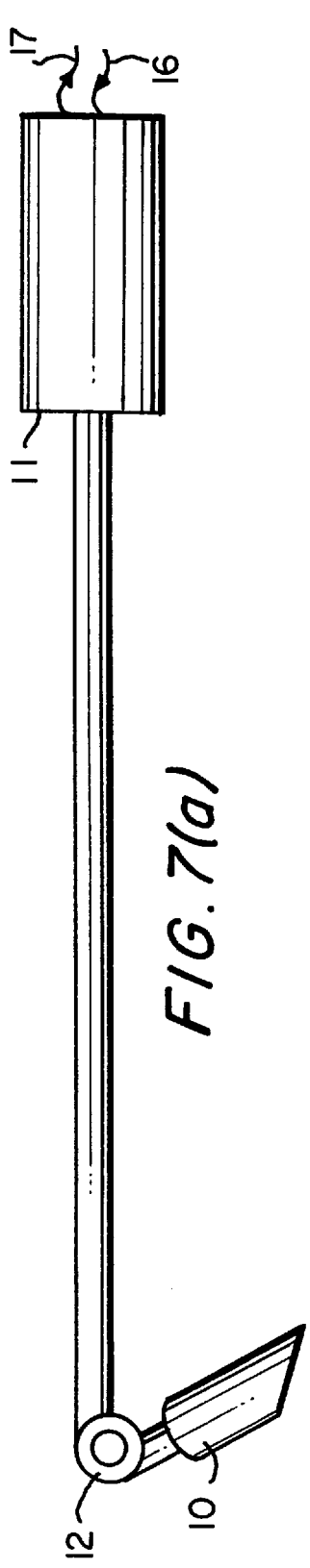
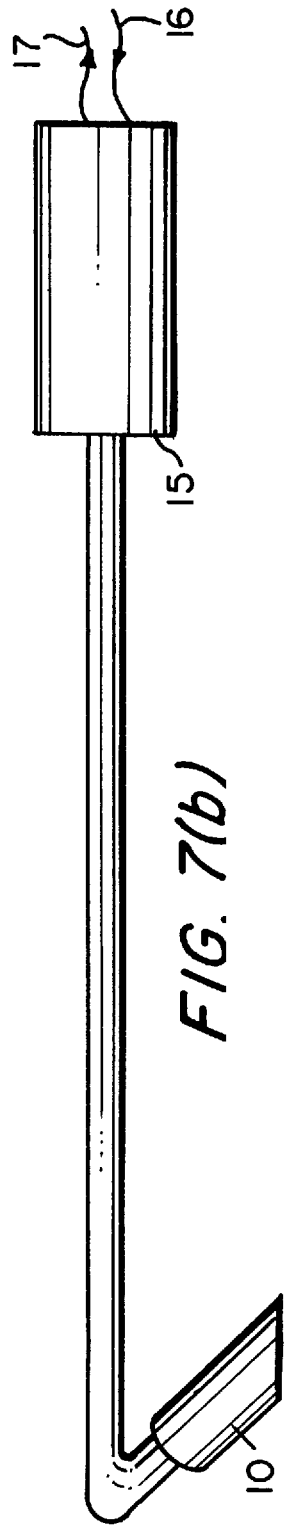
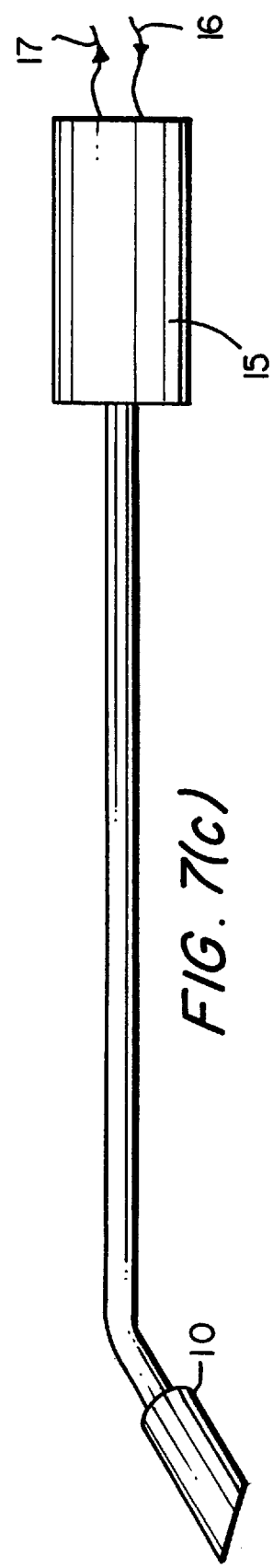

DEVICE AND METHOD FOR THE ULTRASONIC DETECTION OF DENTAL CARIES

BACKGROUND

Dental caries is a disease manifested by local demineralization of the hard tissues of the tooth crown induces by dental plaque. The demineralization process progresses from the outer enamel surface of the crown through the entire thickness of the enamel and into the dentine. Caries lesions of occlusal, buccal and lingual (palatinal) surfaces can be diagnosed by mechanical probing and/or visual inspection. On the other hand, small and medium size lesions of interproximal crown surfaces are hidden by the gingiva and adjacent teeth and have hitherto been identifiable only on radiographs. Although the use of bitewing radiographs is well accepted as an important adjunct in the diagnosis of proximal caries lesions, this method exhibits several weaknesses related to its relative insensitivity and user dependence in terms of technical performance and interpretation [Waggoner W., F. Crall J. J. (1984) Quintessence International 11/1984: 1163–1173]. Furthermore, bitewing radiographs comprise a high proportion of x-rays taken in the dental office. This is in contrast with the current trends in safety standards which support every effort aimed at reducing the exposure to ionizing irradiation. In addition, an alternative technology for the detection of interproximal caries is expected to reduce the environmental pollution and cost associated with the use of x-ray technology.

The potential of ultrasonic technology for the detection of dental caries has been proposed in several instances. It has been shown that the hard tissues of the tooth crown, in particular the outer enamel layer, are highly uniform in their sonic properties among different teeth and individuals [Ng S. Y., Payne P. A., Cartledge N. A., Ferguson M. W., (1989), Arch. Oral Biol. 34: 341–345; Barber F. E., Lees S., Lobene R. R., (1969), Arch. Oral Biol. 14: 745–760]. Using a longitudinal ultrasonic irradiation, a specific profile of ultrasonic echoes is obtained from the enamel surface, dentinoenamel junction and pulpodentinal junction. Changes in this profile have been described in instances of demineralization lesions indicating a substantial difference in the sonic conductivity between sound and demineralized enamel [Ng S. Y., Ferguson M. W. J., Payne P. A., Slater P., (1988), J. Dent 16:201–209; PCT no. WO 95/04506]. These changes result from conversion of the intact enamel to the water rich demineralized material. However, the detection of these lesions is dependent on a direct contact between the ultrasonic probe and the demineralized enamel; such contact cannot be formed in interproximal sites. In addition, echo profiles to longitudinal waves obtained from sound and demineralized tooth crowns are complicated and can be analyzed only by using complex systems.

The present invention relates to a revolutionary approach regarding the use of ultrasonic technology for the detection of dental caries. Rather than transmitting longitudinal ultrasonic waves into the tooth, as in the prior art, the present invention relates to an ultrasonic device that imparts surface ultrasonic waves onto the enamel surface, which then migrate along same. Surface or Rayleigh waves are well known [Cook, E. G., Van Valkenburg H. E., (1954) ASTM-Bull 84]. These waves are generated by an ultrasonic probe in which the longitudinal axis of the piezoelectric crystal, herein defined as an imaginary line passing through the geometrical centre of the crystal surface and perpendicular thereto, lies at an angle substantially smaller than 90° to the tested surface, by virtue of an appropriately designed wedge-like interface. Surface waves migrate uninterruptedly on smooth, flat or curved, contours. Sharp angles, interferences and sonic interfaces present on the surface produce distinct echoes [Krautkraimer J., Krautkrämer H., Ultrasonic Testing of Materials, (1969) Springer-Verlag Berlin Heidelberg New York; pp. 257–271]. The amplitude and shape of these echoes is dependent on the geometry of such interferences. Thus, the interface between a caries lesion and intact enamel may be identified by an echo or reflection of surface ultrasonic waves produced thereat. Since said reflected surface ultrasonic waves have an amplitude substantially greater than the general background level, the profiles of said waves are relatively simple to analyse. Furthermore, since the ultrasonic device of the present invention does not require to be placed directly onto the zone of interest on the tooth surface, it is particularly useful for the detection of caries lesions in areas such as the interproximal site, hitherto inaccessible with ultrasound devices of the prior art.

BRIEF DESCRIPTION OF FIGURES

FIG. 7 shows the device of FIG. 1 fitted with an extension handle.

SUMMARY OF THE INVENTION

A device for the detection of smooth surface lesions of dental caries on a tooth crown surface, comprising an ultrasonic transducer for transmitting ultrasonic waves and receiving ultrasonic wave reflections produced by said lesions, and further comprising an interface operatively connected to said transducer and having a contact surface, said contact surface forming an angle $\alpha$ with a longitudinal axis of the said ultrasonic transducer substantially different from 90°, whereby, when said contact surface is in at least partial contact with said tooth crown surface at said longitudinal axis, ultrasonic waves generated by said ultrasonic transducer are imparted by said interface onto said tooth crown surface as surface ultrasonic waves which migrate along said tooth crown surface, said lesions being identifiable as surface ultrasonic wave reflections produced thereat.

DESCRIPTION

The present invention relates to a device for the detection of smooth surface lesions of dental caries on a tooth crown surface, comprising an ultrasonic transducer for transmitting ultrasonic waves and receiving ultrasonic wave reflections produced by said lesions, and further comprising an interface operatively connected to said transducer and having a contact surface, said contact surface forming an angle $\alpha$ with a longitudinal axis of the said ultrasonic transducer substantially different from 90°. Thus, when said contact surface is in at least partial contact with said tooth crown surface at said longitudinal axis, ultrasonic waves generated by said ultrasonic transducer are imparted by said interface onto said tooth crown surface as surface ultrasonic waves which migrate along said tooth crown surface, said lesions being identifiable as surface ultrasonic wave reflections produced thereat.

Figure 1:
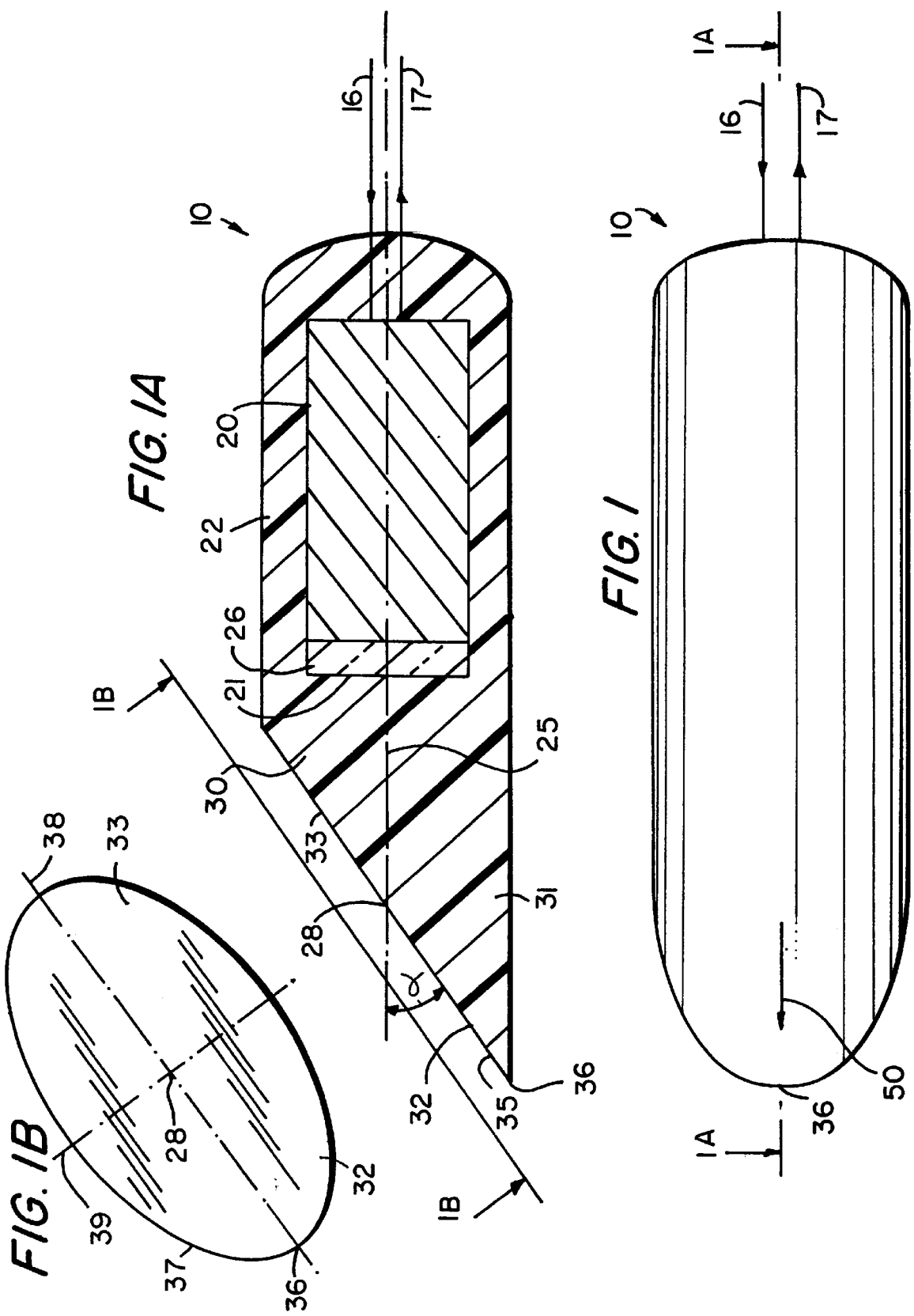
FIG. 1 illustrates the main features of the preferred embodiment of the device according to the present invention.

FIG. 1 depicts the overall concept of the device according to the invention. The said device, designated (10), comprises an ultrasonic transducer (20), comprising a piezoelectric crystal (26), and a wedge-like interface (30) preferably made from polyurethane and having a contact surface (35) operatively connected to said transducer (20). The contact surface (35) forms an angle α with the longitudinal axis (25) of the said ultrasonic transducer (20) substantially different from 90°. The said angle α is thus also the complementary angle to the angle between a plane containing said surface (35) and a plane perpendicular to said axis (25). The longitudinal axis (25) of the transducer (20) is herein defined as an imaginary line passing through the geometrical centre of the forward face (21) of the said piezoelectric crystal (26) and perpendicular thereto.

Said angle α may be determined by the equation:

$$\alpha = [90° - \sin^{-1}(V_L/V_x)] \pm E°$$

where $V_L$ is the longitudinal ultrasound velocity in the interface material, in meters per second, and will thus vary with said material. $V_L$ may be determined for a particular interface material in a manner known in the art. $V_x$ is the surface velocity of surface ultrasonic waves, which, for human enamel, has been determined empirically by the inventors to be of the order of 3143 meters per second, with maximum and minimum measured values of 3416 and 2957 meters per second, respectively. $E°$ is a measure of the deviation from α in degrees wherein at least a major portion of the ultrasonic waves generated by the transducer (20) is imparted as surface ultrasonic waves by said interface (30). Typically, $E°$ may be 10°.

The value of $V_L$ for polyurethane is approximately 1500 meters per second, and thus, an interface made from this material has an angle α of approximately 60°.

Said transducer (20) is capable of generating and transmitting ultrasonic waves and also of receiving ultrasonic reflections, in a manner known in the art.

Typically, ultrasonic waves of frequency in the range of 2 to 20 MHz is provided by said transducer (20).

In a preferred embodiment, said interface (30) comprises part of a housing (22) in which the transducer (20) is located, and the forward—i.e. patient end—face (21) of the said piezoelectric crystal (26) defines the operative transducer end of the said interface (30). Said interface (30) is of circular section at planes perpendicular to said axis (25), so that the contact surface (35), when viewed perpendicular to same, appears as an ellipse (37) having a major axis (38) with leading edge (36) and a minor axis (39). Thus, said contact surface (35) may be divided at said minor axis (39) into two portions (32) and (33), wherein the forward portion (32) lies at an acute angle α to said axis (25), and the rearward portion (33) lies at an obtuse angle (180°−α) to said axis (25). Said leading edge (36) is defined as the intersection point of the major axis (38) or said pseudo-major axis with the periphery (34) of said forward portion (32) of contact surface (35). Alternatively, said interface (30) may have a polygonal or other cross-section at planes perpendicular to said axis (25), wherein the contact surface (35) has a definable shape when viewed in a direction perpendicular thereto, and wherein said definable shape may be attributed with pseudo-major axis and a pseudo-minor axis, said pseudomajor axis originating at a location on said definable shape corresponding to said leading edge (36) as hereinbefore defined and intersecting said axis (25). Thus, said pseudo-minor axis is at right angles to, and coplanar with, said pseudo-major axis and also intersects said axis (25).

Said contact surface (35) may be planar; alternatively, said contact surface (35) may be concave with a concavity having a radius at planes perpendicular to said major axis (38) preferably smaller or equal to the minimum radius of convex curvature of the tooth (90). In embodiments where said contact surface (35) is not planar, angle α is referenced to a plane tangential to said contact surface (35) at its intersection with said axis (25), i.e. at (28). Said contact surface (35) may be rigid; alternatively, said contact surface (35) may be elastically distortable to conform to the profile of the tooth (90), wherein said interface is preferably made from polyurethane or silicone or any other suitable polymeric material.

Preferably, a very small amount of water or oil of the type customarily used in the art is placed between the said contact surface (35) and the tooth surface (95) to moisten the said surfaces and to ensure good contact therebetween.

Figure 2:
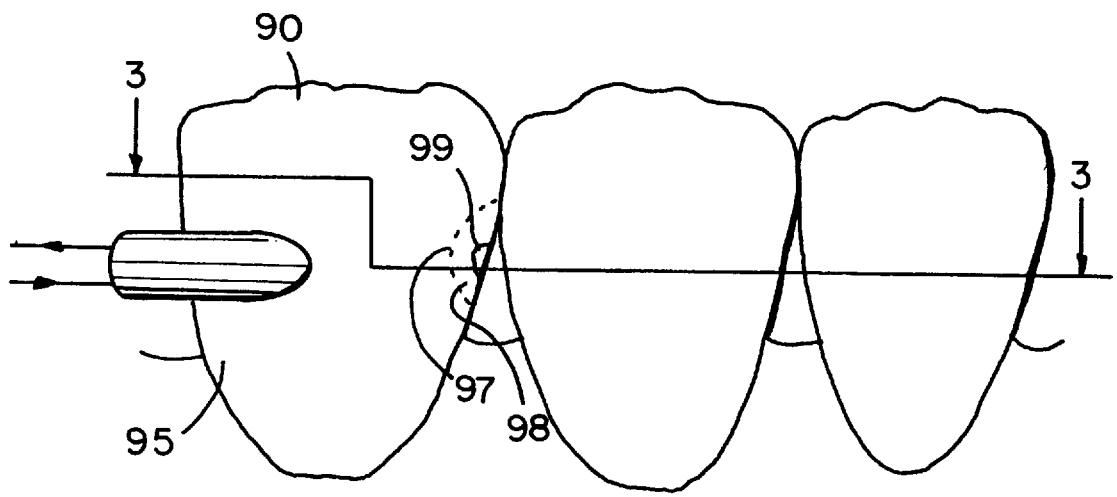
FIG. 2 shows in side view a portion of a dentition, with the device of FIG. 1 in contact with the crown surface of a tooth.
Figure 3:
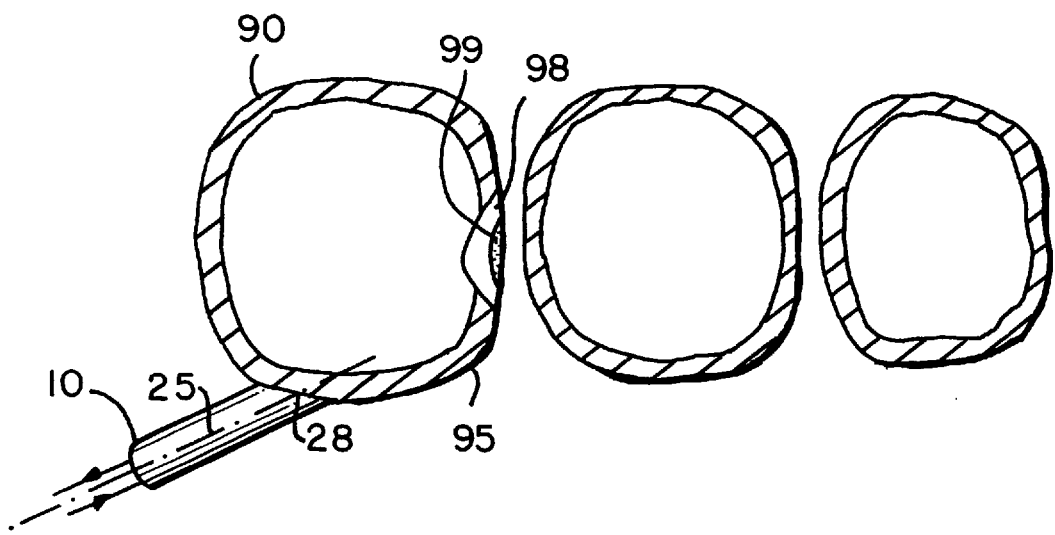
FIG. 3 is cross sectional view of the items shown in FIG. 2 taken along K—K, which represents a coronal section at the level of an interproximal caries lesion.

FIGS. 2 and 3 show a section of a dentition comprising a number of adjacent teeth, wherein surface lesions (99) of dental caries is suspected in an interproximal site (98) of the tooth crown surface (95) of a tooth (90).

According to the present invention, when said contact surface (35) is in at least partial contact at said longitudinal axis (25), i.e. at (28), with the tooth crown surface (95) of a tooth (90), ultrasonic waves imparted by means of said interface (30) onto said tooth crown surface (95) migrate as surface ultrasonic waves along said tooth crown surface (95), departing the said contact surface (35) generally from the leading edge (36) and in a general direction continuous to said major axis (38) or said pseudo-major axis. Said lesions (99), if present, are identifiable as surface ultrasonic wave reflections produced thereat. These reflections are received by said ultrasonic transducer (20) and are converted to corresponding electrical signals, which process is well known in the art.

As already described, the surface waves depart from said contact surface (35) generally from the leading edge (36) and in a general direction continuous to said major axis (38) or said pseudo-major axis. Thus, the device (10) may be oriented on a tooth surface to impart surface waves in a preferred direction. In the preferred embodiment, the device (10) further comprises identifying means whereby the device (10) may be suitably oriented with respect to a zone (97) on the said tooth crown surface (95) for maximising the amplitude of surface ultrasonic wave reflections that may be produced by said lesions (99) that may be present at said zone (97). In the preferred embodiment, said identifying means comprises a suitable targeting mark (50) on said device (10). Examples of a said targeting mark (50) include an arrow or coloured spot on the outer surface of the forward portion (32) of the forward part (31) of said interface (30) comprising said forward portion (32) of said contact surface (35), i.e. close to the said leading edge (36). Thus, an operator's task of orienting the device (10) on the surface (95) of a tooth (90) with respect to a zone (97) is greatly facilitated by being able to direct the targeting mark (50) towards the desired zone (97). In general, said zone (97) is located in the interproximal site (98), though it may be located elsewhere on said tooth crown surface (95).

Figure 4A:
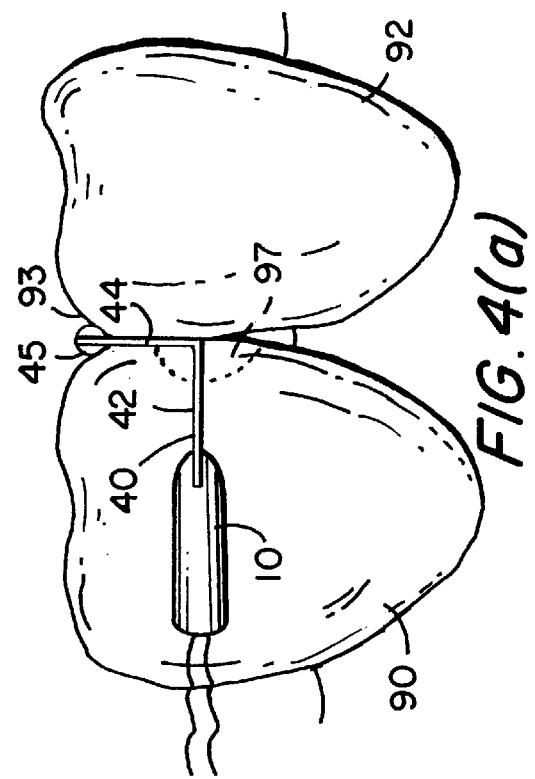
FIG. 4 illustrates adjunct spacing means according to the present invention.
Figure 4B:
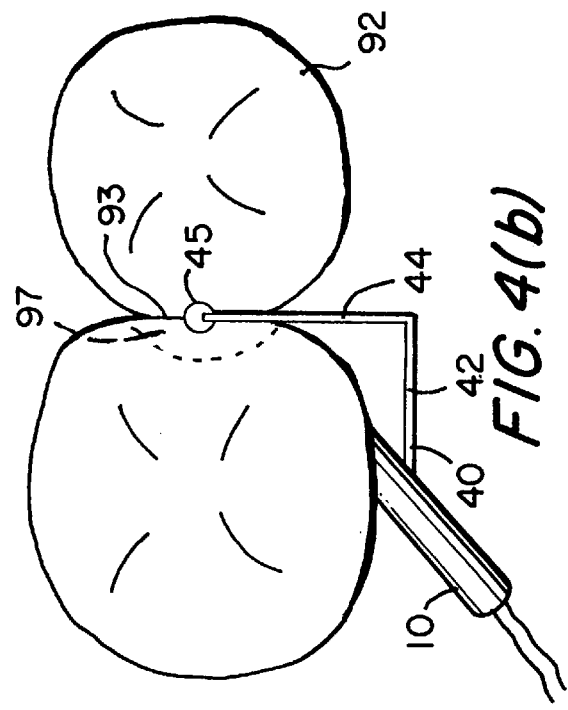
Figure 4C:
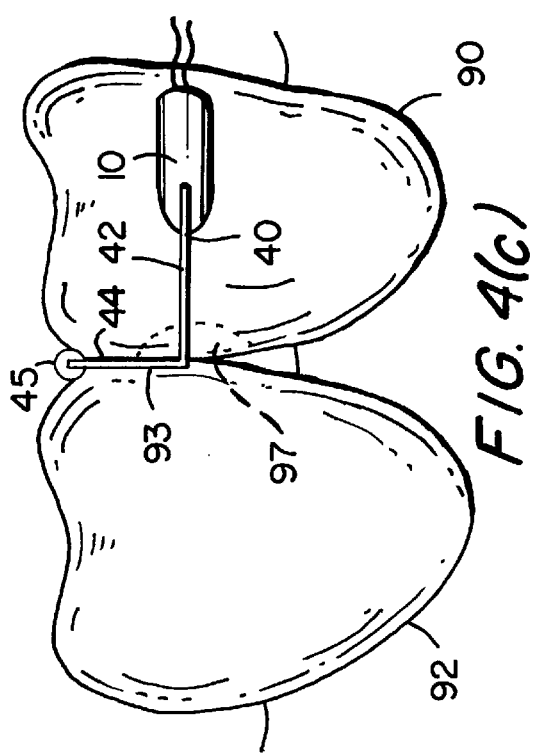
Figure 4D:
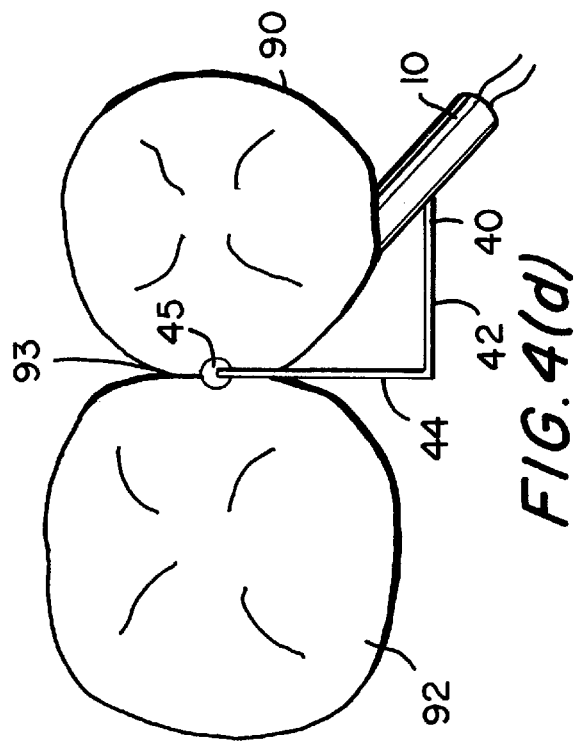

In another embodiment of said device, said identifying means comprises suitable adjunct spacing means (40) placed against the contact point between the examined interproximal surface and an adjacent tooth, for providing a predetermined spatial relationship between said device (10) and said zone (97). FIG. 4 illustrates an example of said spacing means (40), comprising a horizontal spacing member (42) rigidly attached at one end thereof to said device (10) in proximity to said leading edge (36) thereof, the other end of said spacing member (42) being rigidly attached to a transverse member (44) at one end thereof. Said member (44) is suitably shaped so that the other end (45) thereof may hook onto or press against the contact point (93) between said tooth (90) and an adjacent tooth (92), such that no part of said members (42) or (44) are in contact with the tooth surface (95) anywhere close to an imaginary direct line between said leading edge (36) and said desired zone (97). An operator would thus place the said end (45) of the spacing means (40) against the contact point (93) between two teeth, the said device (10) being automatically oriented on one tooth thereof towards the corresponding desired zone (97). Optionally, said spacing means (40) may be left-handed, as shown in FIG. 4(a) and (b), or right-handed, as shown in FIGS. 4(c) and (d). Preferably, though, said transverse member (44) may be modified, as for example by incorporating a hinging means about its contact point with said horizontal member (42), so that the spacing means may be used alternately either in the right-handed sense or in the left-handed sense.

Figure 5:
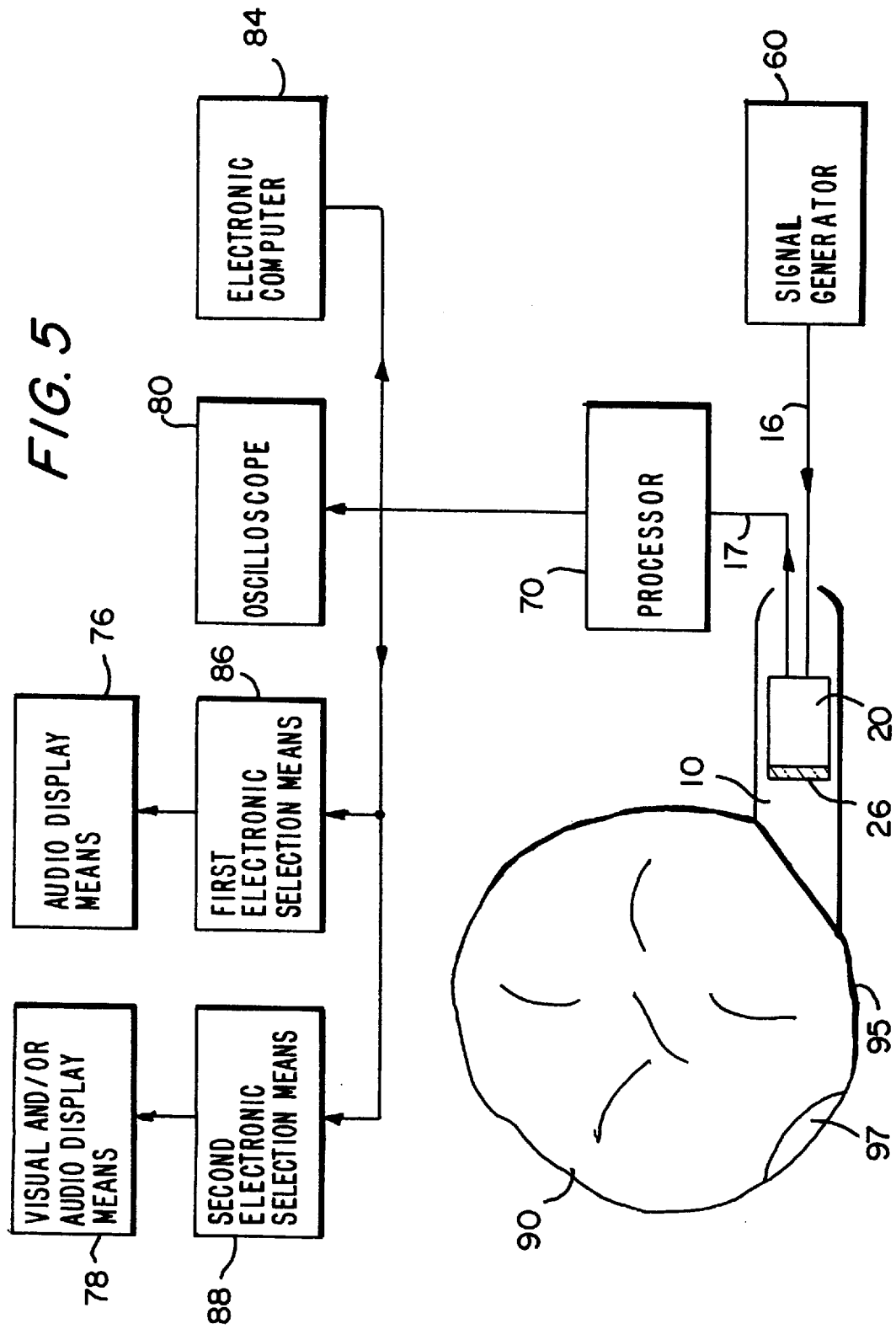
FIG. 5 illustrates the device of FIG. 1 and peripheral components.

FIG. 5 shows schematically the said device (10) and peripheral components. A signal generator (60) comprising a suitable power source is electrically connected to said transducer (20), which is then able to impart ultrasonic surface waves along the surface (95) of the tooth (90) as hereinbefore described. Surface waves reflections received by said transducer are converted into corresponding electrical signals which are then amplified and processed in a processor (70). Peripheral electronic means such as oscilloscope (80) is operatively connected to said device (10) and may be used for displaying the profile of said surface ultrasonic wave reflections received by said device (10) in a manner known in the art. Said electrical signals may also be channeled to an electronic computer (84) for further analysis. The said oscilloscope (10) may typically display a sequence of echoes of varying amplitude, "A", as a function of time-of-flight, "t", hereinafter referred to as an A-t scan. Time-of-flight relates to a time-separation on the display which may be equated to velocity and therefore real distance along the tooth surface (95). This form of display is relatively easy to interpret by a user, typically a dentist for example, as the occurrence of an echo of substantial amplitude at a particular time-of-flight, relative to background amplitudes at other times-of-flight, indicates the existence of a lesion (99) at a distance along the tooth surface from the device (10) corresponding to this time-of-flight.

Figure 6A:
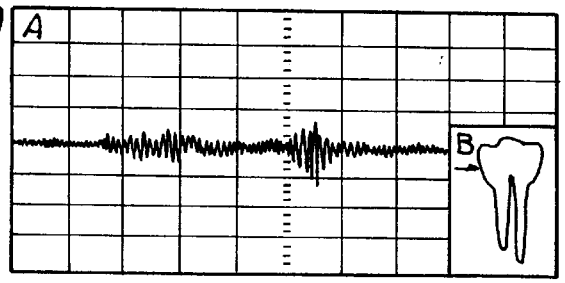
FIG. 6 illustrates typical reflections of surface ultrasonic waves obtained with teeth having various depths of caries lesions therein.
Figure 6B:
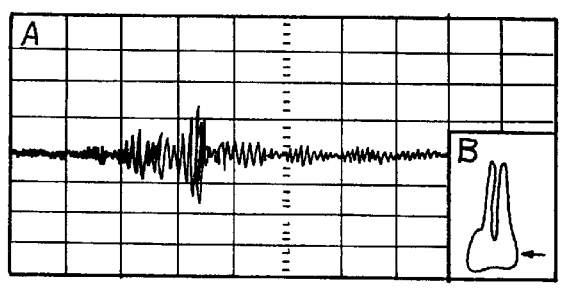
Figure 6C:
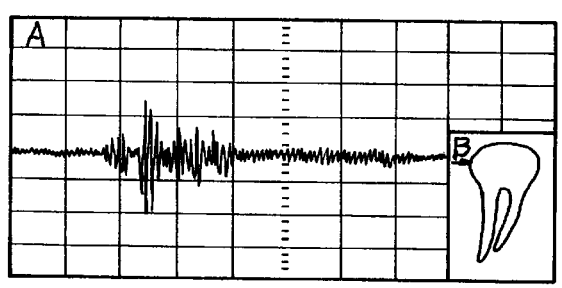
Figure 6D:
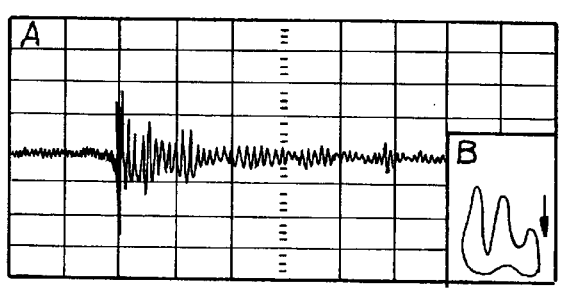
Figure 6E:
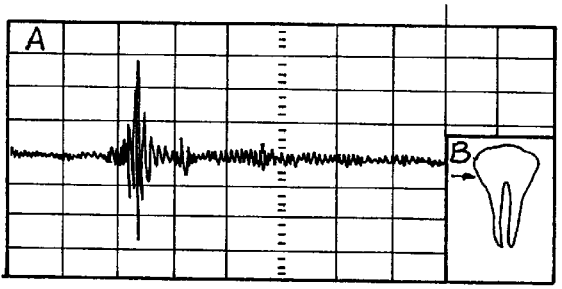
Figure 6F:
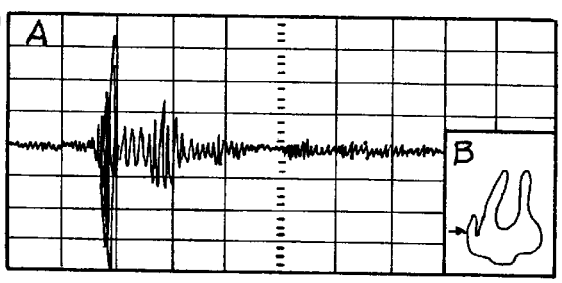

The amplitude of reflected ultrasonic waves from lesions may be correlated with the depth of caries lesions. FIG. 6(a) to 6(f) shows the A-t scans that were obtained by using a device (10) according to the present invention on six teeth having varying degrees of caries lesions. FIG. 6(a) relates to a tooth having a small whitespot lesion; FIGS. 6(b) and 6(c) relate to a whitespot and a white-and-brownspot lesion; FIGS. 6(d),6(e) and 6(f) relate to caries lesions with surface cavitation. Table I tabulates the amplitudes of the reflected ultrasonic surface waves relating to FIGS. 6(a) to 6(f), and also shows corresponding radiolucency produced by interproximal caries on each tooth, said radiolucency being scored according to the German Rating System (GRS) [Marthaler T. M., (1970) Caries Res, 4: 224–242] as follows:

0: no radiolucency evident
1: radiolucency limited to outer one half of enamel
2: radiolucency evident in inner one half of enamel
3: radiolucency evident in outer one half of dentine
4: radiolucency penetrates into inner one half of dentine

TABLE I

| Ultrasonic and radiographic scores of caries lesion relating to FIGS. 6(a) to 6(f) | | |
|---|---|---|
| FIG. No. | Echo amplitude (mV) | Radiolucency extent (GRS) |
| 6a | 62 | 0 |
| 6b | 152 | 2 |
| 6c | 176 | 2 |
| 6d | 240 | 3 |
| 6e | 292 | 3 |
| 6f | 380 | 3 |

Thus, it is possible to construct amplitude bands, each having an upper and a lower threshold level, wherein each band corresponds to a radiolucency extent, which in turn relates to the extent of caries lesion. Optionally, then, the said device (10) further comprises first electronic selection means (86), suitably connected thereto, for generating electronic signals corresponding to surface ultrasonic wave reflections having an amplitude within at least one set of predetermined upper and lower thresholds in a manner known in the art. Said differently, said selection means (86) acts as a filter and generates a discrete electronic signal corresponding to a particular amplitude band when the amplitude of a surface ultrasonic wave reflection falls within said band. Said selection means (86) may further comprise visual and/or audio display means (76) for displaying said electronic signals in a manner known in the art such as a LCD counter wherein the numbers "0", "1", "2" etc. may be displayed according to whether the signal generated by said selection means (86) corresponds to an amplitude band having a similar value of radiolucency extent correlated thereto.

Similarly, it is also possible to construct time of flight bands, each having an upper and a lower threshold level, wherein each band corresponds to a region on the tooth surface (95) at a corresponding distance from the device (10). Optionally, then, the said device (10) further comprises second electronic selection means (88), suitably connected thereto, for generating electronic signals corresponding to surface ultrasonic wave reflections having significantly higher amplitude than background levels wherein the time of flight corresponding to said higher amplitude falls within at least one set of predetermined upper and lower thresholds in a manner known in the art. Said differently, said selection means (88) acts as a filter and generates a discrete electronic signal corresponding to a particular time of flight band, and therefore a particular region on the tooth surface, when the amplitude of a surface ultrasonic wave reflection sufficiently higher than background levels falls within said band. Thus an operator such as a dentist, for example, may position said device (10) at a predetermined distance interval, say 4 mm from a desired zone (97), and, if reflections of ultrasonic waves are detected, said operator may thus ensure that these reflections originate from said zone, as the said selection means (88) would be set to generate a discrete signal when the time of flight of the reflected waves corresponding to, say, 3.5 mm–4.5 mm. The precise upper and lower threshold levels for said time of flight bands may differ for different types of teeth, e.g. molars incisors and canines. Said means (88) may further comprise visual and/or audio display means (78) for displaying said electronic signals corresponding to each type of tooth in a manner known in the art such as a LCD counter wherein the characters "M", "I", "C" etc. may be displayed according to whether the signal generated by said selection means (88) corresponds to a standard time of flight expected on the type of tooth being tested. Optionally, the said selection means (88) may be preset by the user according to a preferred set of upper and lower threshold levels for time of flight.

Optionally, said device (10) further comprises a suitable extension handle (15) releasably attached to or integral with said device (10). Said handle (15) may be similar to handles known in the art and used by dentists to reach deep molars. Said handle (15) is preferably made from a rigid medically compatible material such as stainless steel or a suitable plastic material, examples of which are known in the art, and is preferably hollow to allow input and output cables, (16) and (17) respectively, to said transducer (20) to be routed therein.

Optionally, said handle (15) is mounted to said device (10) via suitable hinge means (12), wherein the said handle (15) may rotate relative to said device (10) varying the angle φ therebetween, as illustrated in FIG. 7(*a*), wherein angle φ may be an acute or an obtuse angle. Said hinge means (12) are known in the art and may comprise a two-dimensional hinge or a universal joint, for example.

Optionally, said device (10) may be mounted at an acute angle β or alternatively at an obtuse angle γ relative to said handle (15), as illustrated in FIGS. 7(*b*) and 7(*c*) respectively.

The present invention also relates to a method for the detection of smooth surface lesions of dental caries on a tooth crown surface, comprising the steps of:

(i) providing a device comprising an ultrasonic transducer for transmitting ultrasonic waves and receiving ultrasonic wave reflections produced by said lesions, said device further comprising an interface operatively connected to said transducer, said interface having a contact surface forming an angle α with a longitudinal axis of the said ultrasonic transducer substantially different from 90°;

(ii) positioning said contact surface in at least partial contact with respect to said tooth crown surface at said longitudinal axis;

(iii) generating ultrasonic waves by said transducer, wherein said ultrasonic waves are imparted onto said tooth crown surface as surface ultrasonic waves which migrate along said tooth crown surface, (iv) identifying said lesions as surface ultrasonic wave reflections produced thereat.

The present invention also relates to the method for the detection of smooth surface lesions of dental caries on a tooth crown surface hereinbefore described, wherein said angle α is obtained from the equation:

$$\alpha = [90° - \sin^{-1}(V_L/3143)] \pm 10°$$

wherein $V_L$ is the longitudinal velocity in the interface material in meters per second. Preferably, said angle α is between 20° and 70°.

The present invention also relates to the method for the detection of smooth surface lesions of dental caries on a tooth crown surface hereinbefore described, wherein said contact surface may be planar, or, alternatively, concave. Furthermore, said interface may be rigid, and said contact surface may be elastically distortable, wherein said interface is preferably made from polyurethane or silicone or any other suitable polymeric material.

The present invention also relates to the method for the detection of smooth surface lesions of dental caries on a tooth crown surface hereinbefore described, wherein said device further comprises identifying means whereby said device may be suitably oriented with respect to a zone on said tooth crown surface for substantially maximising the amplitude of surface ultrasonic wave reflections that may be produced by said lesions that may be present at said zone. Said identifying means may comprise a suitable targeting mark on said device or, alternatively, said identifying means may comprise suitable adjunct spacing means for providing a predetermined spatial relationship between said device and said zone.

The present invention also relates to the method for the detection of smooth surface lesions of dental caries on a tooth crown surface hereinbefore described, further comprising the step of providing peripheral electronic means, as hereinbefore described for example, for displaying the profile of said surface ultrasonic wave reflections received by said device. Said peripheral electronic means are operatively connected to said device.

The present invention also relates to the method for the detection of smooth surface lesions of dental caries on a tooth crown surface hereinbefore described, further comprising the step of providing first electronic selection means, as hereinbefore described, for generating electronic signals corresponding to surface ultrasonic wave reflections having an amplitude within at least one set of predetermined upper and lower thresholds. Said first electronic selection means may be operatively connected to said device directly. Alternatively, said first electronic selection means may be operatively connected to said device via said peripheral electronic means. Preferably, said electronic selection means further comprise visual and/or audio display means, as hereinbefore described for example, for displaying said electronic signals.

The present invention also relates to the method for the detection of smooth surface lesions of dental caries on a tooth crown surface hereinbefore described, further comprising the step of providing second electronic selection means, as hereinbefore described for example, for generating electronic signals corresponding to surface ultrasonic wave reflections having significantly greater amplitude than background levels, wherein the time of flight of said wave reflections is within at least one set of predetermined upper and lower thresholds. Said second electronic selection means may be operatively connected to said device directly. Alternatively, said second electronic selection means may be operatively connected to said device via said peripheral electronic means or via said first electronic selection means. Preferably, said electronic selection means further comprise visual and/or audio display means, as hereinbefore described for example, for displaying said electronic signals.

The present invention also relates to the method for the detection of smooth surface lesions of dental caries on a tooth crown surface hereinbefore described, further comprising the step of providing a suitable extension handle releasably attached to or integral with said device, as hereinbefore described for example. Preferably. said handle is mounted to said device via suitable hinge means, as hereinbefore described for example, wherein the said handle may rotate relative to said device varying the angle therebetween. The angle between said device and said handle may be an acute angle, or alternatively, an obtuse angle.

Thus, the device (10) may be used as follows. A user positions the device onto the crown surface (95) of a tooth (90), such that the contact surface (35) is in at least partial contact with the surface (95) at the axis (25), i.e., at (28). Typically, a small quantity of water or oil of the type customarily used in the art is placed between the contact surface (35) and the tooth surface (95). The leading edge (36) of the interface (30) is then oriented towards the zone (97) where caries lesions are suspected, usually the interproximal site (98), but may be elsewhere on the surface (95). The user may be optionally aided in orienting the device (10) by means of a target (50) or adjunct spacing means (40), as hereinbefore described. Ultrasonic waves are then produced by the transducer (20) in a manner known in the art, and then imparted to the tooth surface (95) as surface ultrasonic waves by means of the interface (30). These surface ultrasonic waves migrate along the surface generally towards the zone (97), and if they encounter a lesion (99), surface ultrasonic wave reflections are produced thereat. These surface ultrasonic wave reflections are then received by the transducer (20) and may then be processed and displayed and/or selected as hereinbefore described to identify to the user the presence of a lesion, and, optionally, to indicate the depth thereof.

Although only a few embodiments have been described in detail in the foregoing description, the present invention is not limited thereto and is only defined by the scope of the claims.

We claim:

1. A device for the detection of smooth surface lesions of dental caries on a tooth crown surface, comprising an ultrasonic transducer for transmitting ultrasonic waves and receiving ultrasonic wave reflections produced by said lesions, and further comprising an interface operatively connected to said transducer and having a contact surface, said contact surface forming an angle $\alpha$ with a longitudinal axis of the said ultrasonic transducer substantially different from 90°, whereby, when said contact surface is in at least partial contact with said tooth crown surface at said longitudinal axis, ultrasonic waves generated by said ultrasonic transducer are imparted by said interface onto said tooth crown surface as surface ultrasonic waves which migrate along said tooth crown surface, said lesions being identifiable as surface ultrasonic wave reflections produced thereat.

2. A device according to claim 1, wherein said angle is obtained from the equation:

$$\alpha = [90° - \sin^{-1}(V_L/V_x)] \pm E°$$

wherein $V_L$ is the longitudinal velocity in the interface material and $V_x$ is the surface velocity of surface ultrasonic waves for human enamel, and E is a measure of deviation from $\alpha$ wherein at least a major portion of the ultrasonic waves generated by the said transducer is imparted as surface ultrasonic waves by said interface.

3. A device according to claim 1, wherein said angle $\alpha$ is between 20° and 70°.

4. A device according to claim 1, wherein said contact surface is planar.

5. A device according to claim 1, wherein said contact surface is concave.

6. A device according to claim 1, wherein said interface is rigid.

7. A device according to claim 1, wherein said contact surface is elastically distortable.

8. A device according to claim 7 wherein said interface is made from polyurethane or silicone or any other suitable polymeric material.

9. A device according to claim 1, further comprising identifying means whereby said device may be suitably oriented with respect to a zone on said tooth crown surface for substantially maximising the amplitude of surface ultrasonic wave reflections that may be produced by said lesions that may be present at said zone.

10. A device according to claim 9, wherein said identifying means comprise a suitable targeting mark on said device.

11. A device according to claim 9, wherein said identifying means comprise suitable adjunct spacing means for providing a predetermined spatial relationship between said device and said zone.

12. A device according to claim 1, further comprising peripheral electronic means, operatively connected to said device, for displaying the profile of said surface ultrasonic wave reflections received by said device.

13. A device according to claim 1, further comprising electronic selection means, suitably connected to said device, for generating electronic signals corresponding to surface ultrasonic wave reflections having an amplitude within at least one set of predetermined upper and lower thresholds.

14. A device according to claim 1, further comprising electronic selection means, suitably connected to said device, for generating electronic signals corresponding to surface ultrasonic wave reflections having significantly greater amplitude than background levels, wherein the time of flight of at least one of each of said wave reflections is within at least one set of predetermined upper and lower thresholds.

15. A device according to claim 13, further comprising visual and/or audio display means for displaying said electronic signals.

16. A device according to claim 14, further comprising visual and/or audio display means for displaying said electronic signals.

17. A device according to claim 1, further comprising a suitable extension handle releasably attached to or integral with said device.

18. A device according to claim 17, wherein said handle is mounted to said device via suitable hinge means, wherein the said handle may rotate relative to said device varying the angle therebetween.

19. A device according to claim 17, wherein the angle between said device and said handle is an acute angle.

20. A device according to claim 18, wherein the angle between said device and said handle is an acute angle.

21. A device according to claim 17, wherein the angle between said device and said handle is an obtuse angle.

22. A device according to claim 18, wherein the angle between said device and said handle is an obtuse angle.

23. A method for the detection of smooth surface lesions of dental caries on a tooth crown surface, comprising the steps of:

(i) providing a device comprising an ultrasonic transducer for transmitting ultrasonic waves and receiving ultrasonic wave reflections produced by said lesions, said device further comprising an interface operatively connected to said transducer, said interface having a contact surface forming an angle $\alpha$ with a longitudinal axis of said ultrasonic transducer substantially different from 90°;

(ii) positioning said contact surface in at least partial contact with respect to said tooth crown surface at said longitudinal axis;

(iii) generating said ultrasonic waves by said transducer, wherein said ultrasonic waves are imparted onto said tooth crown surface as surface ultrasonic waves which migrate along said tooth crown surface; and (iv) identifying said lesions as surface ultrasonic wave reflections produced thereat.

24. A method according to claim 23, wherein said angle α is obtained from the equation:

$$\alpha=[90°-\sin^{-1}(V_L/V_x)]\pm E°$$

wherein $V_L$ is the longitudinal velocity in the interface material and $V_x$ is the surface velocity of surface ultrasonic waves for human enamel, and E is a measure of deviation from α wherein at least a major portion of the ultrasonic waves generated by the said transducer is imparted as surface ultrasonic waves by said interface.

25. A method according to claim 23, wherein said angle α is between 20° and 70°.

26. A method according to claim 23, wherein said contact surface is planar.

27. A method according to claim 23, wherein said contact surface is concave.

28. A method according to claim 23, wherein said interface is rigid.

29. A method according to claim 23, wherein said contact surface is elastically distortable.

30. A method according to claim 29 wherein said interface is made from polyurethane or silicone or any other suitable polymeric material.

31. A method according to claim 23, wherein said device further comprises identifying means whereby said device may be suitably oriented with respect to a zone on said tooth crown surface for substantially maximising the amplitude of surface ultrasonic wave reflections that may be produced by said lesions that may be present at said zone.

32. A method according to claim 31, wherein said identifying means comprise a suitable targeting mark on said device.

33. A method according to claim 31, wherein said identifying means comprise suitable adjunct spacing means for providing a predetermined spatial relationship between said device and said zone.

34. A method according to claim 23, further comprising the step of providing peripheral electronic means, operatively connected to said device, for displaying the profile of said surface ultrasonic wave reflections received by said device.

35. A method according to claim 23, further comprising the step of providing electronic selection means, suitably connected to said device, for generating electronic signals corresponding to surface ultrasonic wave reflections having an amplitude within at least one set of predetermined upper and lower thresholds.

36. A method according to claim 23, further comprising the step of providing electronic selection means, suitably connected to said device, for generating electronic signals corresponding to surface ultrasonic wave reflections having significantly greater amplitude than background levels, wherein the time of flight of at least one of each of said wave reflections is within at least one set of predetermined upper and lower thresholds.

37. A method according to claim 35, wherein said electronic selection means further comprises visual and/or audio display means for displaying said electronic signals.

38. A method according to claim 36, wherein said second electronic selection means further comprises visual and/or audio display means for displaying said electronic signals.

39. A method according to claim 23, wherein said device further comprises a suitable extension handle releasably attached to or integral with said device.

40. A method according to claim 39, wherein said handle is mounted to said device via suitable hinge means, wherein the said handle may rotate relative to said device varying the angle therebetween.

41. A method according to claim 39, wherein the angle between said device and said handle is an acute angle.

42. A method according to claim 40, wherein the angle between said device and said handle is an acute angle.

43. A method according to claim 39, wherein the angle between said device and said handle is an obtuse angle.

44. A method according to claim 40, wherein the angle between said device and said handle is an obtuse angle.

45. A device for the detection of smooth surface lesions of dental caries on a tooth crown surface, comprising an ultrasonic transducer for transmitting ultrasonic waves and receiving ultrasonic wave reflections produced by said lesions, and further comprising an interface operatively connected to said transducer and having a contact surface, said contact surface forming an angle α with a longitudinal axis of the said ultrasonic transducer substantially different from 90°, whereby, when said contact surface is in at least partial contact with said tooth crown surface at said longitudinal axis, ultrasonic waves generated by said ultrasonic transducer are imparted by said interface onto said tooth crown surface as surface ultrasonic waves which migrate along said tooth crown surface, said lesions being identifiable as surface ultrasonic wave reflections produced thereat, and wherein said angle α is obtained from the equation:

$$\alpha=[90°-\sin^{-1}(V_L/V_x)]\pm E°$$

wherein $V_L$ is the longitudinal velocity in the interface material and $V_x$ is the surface velocity of surface ultrasonic waves for human enamel, and E is a measure of the deviation from α wherein at least a major portion of the ultrasonic waves generated by the said transducer is imparted as surface ultrasonic waves by said interface.

46. A method for the detection of smooth surface lesions of dental caries on a tooth crown surface, comprising the steps of:

(i) providing a device comprising an ultrasonic transducer for transmitting ultrasonic waves and receiving ultrasonic wave reflections produced by said lesions, said device further comprising an interface operatively connected to said transducer, said interface having a contact surface forming an angle α with a longitudinal axis of said ultrasonic transducer substantially different from 90°;

(ii) positioning said contact surface in at least partial contact with respect to said tooth crown surface at said longitudinal axis;

(iii) generating said ultrasonic waves by said transducer, wherein said ultrasonic waves are imparted onto said tooth crown surface as surface ultrasonic waves which migrate along said tooth crown surface; and (iv) identifying said lesions as surface ultrasonic wave reflections produced thereat, and wherein said angle $\alpha$ is obtained from the equation:

$$\alpha = [90° - \sin^{-1}(V_L/V_x)] \pm E°$$

wherein $V_L$ is the longitudinal velocity in the interface material and $V_x$ is the surface velocity of surface ultrasonic waves for human enamel, and E is a measure of deviation from $\alpha$ wherein at least a major portion of the ultrasonic waves generated by the said transducer is imparted as surface ultrasonic waves by said interface.

* * * * *